United States Patent [19]

Johs et al.

[11] Patent Number: 5,504,582

[45] Date of Patent: *Apr. 2, 1996

[54] SYSTEM AND METHOD FOR COMPENSATING POLARIZATION-DEPENDENT SENSITIVITY OF DISPERSIVE OPTICS IN A ROTATING ANALYZER ELLIPSOMETER SYSTEM

[75] Inventors: Blaine D. Johs; Shakil A. Pittal; Steven E. Green; John A. Woollam; David W. Doerr; Reed A. Christenson, all of Lincoln, Nebr.

[*] Notice: The portion of the term of this patent shall not extend beyond the expiration date of Pat. No. 5,373,359.

[73] Assignee: J. A. Woollam Co. Inc., Lincoln, Nebr.

[21] Appl. No.: 339,834

[22] Filed: Nov. 14, 1994

Related U.S. Application Data

[63] Continuation-in-part of Ser. No. 265,325, Jun. 24, 1994, Pat. No. 5,373,359.

[51] Int. Cl.⁶ .................................................. G01N 21/21
[52] U.S. Cl. .................................. 356/369; 250/225
[58] Field of Search ................................ 356/364, 365, 356/366, 367, 368, 369; 250/225

[56] References Cited

U.S. PATENT DOCUMENTS

| | | | |
|---|---|---|---|
| 2,837,959 | 6/1958 | Saunderson et al. | |
| 3,846,024 | 11/1974 | Turner | 356/80 |
| 3,880,524 | 4/1975 | Dill et al. | 356/118 |
| 4,042,302 | 8/1977 | Wentz | 356/364 |
| 4,227,079 | 10/1980 | Duher et al. | 250/231 |
| 4,571,074 | 2/1986 | Thevenon | 356/51 |
| 4,606,641 | 8/1986 | Yamada et al. | 356/369 |
| 4,837,603 | 6/1989 | Hayashi | 356/369 |
| 5,076,696 | 12/1991 | Cohn et al. | 356/369 |
| 5,329,357 | 7/1994 | Bernoux et al. | 356/369 |
| 5,373,359 | 12/1994 | Woollam et al. | 356/328 |

FOREIGN PATENT DOCUMENTS

| | | |
|---|---|---|
| 49822 | 3/1982 | Japan . |
| 8300257 | 1/1983 | WIPO . |

OTHER PUBLICATIONS

Retardation Plates—Melles Griot Mht Sheets pp. 14-28-14-31.

Real-Time monitoring and control during MOVPE growth of CdTe using multiwavelength ellipsometry-Johs et al., Thin Solid Films 233 (1993).

Correction for nonlinearity and polarization-Dependent sensitivity in The detection system of rotating analyzer ellipsometers, Russev, App. Optic, vol 28, No. 8, 1989.

Regression calibration method for rotating elements ellipsometers Johs, Thin Solid Films 234 (1993).

Analysis for a novel ellipsometric Technique with special advantages for infrared spectroscopy, Stabia et al., J. Opt. Soc. for Am. 65, 25 (1975).

Automatic rotating element ellipsometers: Calibration, operation, and real-time applications, Rev. Sci. Instrum, 61 (8) Aug. 1990, by Collins.

Automated Ellipsometer, Edwards & Hauge, IBM Tech. Disclosure Bulletin vol. 18, No. 6, Nov. 1975.

*Primary Examiner*—Hoa Q Pham
*Attorney, Agent, or Firm*—James D. Welch

[57] ABSTRACT

An ellipsometer system which includes a pivotal dispersive optics positioned to receive polychromatic light from an analyzer thereof, without further focusing after reflection from a substrate system, is presented. In addition, a stationary compensator, positioned between an analyzer and the dispersive optics, which serves to reduce detector element polarization dependent sensitivity to light entering thereto after it interacts with the dispersive optics, is disclosed. The use of a light fiber to carry light from a source thereof, to a polarization state generator, is also disclosed. The method of the present invention can include application of mathematical correction factors to, for instance, substrate system characterizing PSI and DELTA values, or Fourier ALPHA and BETA coefficients.

20 Claims, 1 Drawing Sheet

SYSTEM AND METHOD FOR COMPENSATING POLARIZATION-DEPENDENT SENSITIVITY OF DISPERSIVE OPTICS IN A ROTATING ANALYZER ELLIPSOMETER SYSTEM

The present application is Continuation-In-Part of application 08/265,325. filed Jun. 24, 1994, now U.S. Pat. No. 5,313,359.

TECHNICAL FIELD

The present invention relates to ellipsometer systems and methods of use. More particularly the present invention is a system and method of use for compensating and correcting polarization-dependent sensitivity in rotating analyzer ellipsometer systems utilizing a stationary compensator.

BACKGROUND

Null and spectroscopic ellipsometer systems for use in investigation and characterization of physical and optical properties of substrate systems are well known. Briefly, such systems operate by monitoring changes effected in the polarization state of a beam of light when said beam of light is caused to interact with a substrate system. Spectroscopic ellipsometer systems, including those which utilize phase modulation and Rotating Analyzers, (ie. rotating analyzer ellipsometer systems, hereinafter (RAE)), are widely applied because they provide improved theoretical precision and high optical efficiency, hence, can be utilized with weaker polychromatic sources of light as compared to null ellipsometer systems. Spectroscopic ellipsometer systems are also faster and easier to use. However, use of spectroscopic ellipsometer systems requires increased attention to compensation necessitated by, for instance, Polarization-Dependent Sensitivity, (hereinafter, (PDS)) in response to applied polychromatic light. Compensation of (PDS) can be approached in two mathematically oriented ways, one of which requires correction of numerous raw data points obtained during investigation of a substrate system by a spectroscopic ellipsometer system, (eg. an RAE), and the second of which applies correction factors to, for instance, Fourier Coefficients, (termed ALPHA and BETA), derived by application of Fourier Analysis to said numerous raw data points. Of said approaches, the second is generally easier to perform and is preferred.

To understand the second approach to mathematically compensating (PDS) it must be appreciated that the end goal of applying ellipsometry to a substrate system is simultaneous characterization of the physical and optical properties of said substrate system. Two ellipsometric constant, (at a particular light beam wavelength and angle of incidence on said substrate), parameters, PSI and DELTA serve to provide said characterization. Calculation of PSI and DELTA, however, is typically intermediated by the calculation of Fourier Coefficients, ALPHA and BETA, as alluded to above. Said Fourier Coefficients, ALPHA and BETA, are related to PSI and DELTA by known mathematical relationships. Briefly, to compensate for system (PDS), ALPHA and BETA can be corrected prior to application of the mathematical relationships which interrelate the Fourier Coefficients ALPHA and BETA, to PSI and DELTA. It is noted that ALPHA and BETA correction factors are typically derived during an ellipsometer system calibration procedure. It is mentioned that direct correction of PSI and DELTA is a variation on said mathematical approach.

As mentioned, PSI and DELTA are constants of a substrate system, but as also mentioned, said constants vary with the wavelength of a beam of light applied to a substrate system by an ellipsometer system. This is because ellipsometer system elements, (eg. dispersive optics), as well as investigated substrate systems, typically respond differently to different wavelengths of light. (Note, see the Disclosure of the Invention and Detailed Description Sections in this Disclosure for insight as to the elements, and their configuration, which comprise a typical ellipsometry system). As a result, an ellipsometer system which performs a substrate system analysis at a multiplicity of wavelengths must provide appropriate ALPHA and BETA (PDS) correction factors for each of said multiplicity of wavelengths utilized, (assuming the second approach to compensating (PDS) identified above is utilized).

Continuing, it is to be appreciated that while compensation can be accomplished based upon a purely mathematical approach, correction factors can become a significant percentage of an ALPHA or BETA value at certain corresponding PSI and DELTA values. When this occurs, application of a correction factor can result in relatively small corrected ALPHA and/or BETA values, which values can be on the order of system background noise. This results in reduced sensitivity, (ie. reduced ability to calculate accurate PSI and DELTA values from said corrected ALPHA and BETA values), at said certain corresponding PSI and DELTA values. It should then be apparent that a system element which would reduce the magnitude of required ALPHA and BETA correction factors would provide utility. A similar situation exists when PSI and DELTA are directly corrected.

It is also mentioned that (RAE's) often comprise elements, (eg. photodetectors), which react nonlinearly with respect to different intensities and wavelengths of light. The above outlined mathematical approach to compensation can be used in such (RAE's) to simultaneously compensate both (PDS) and said nonlinearities.

Continuing, the present invention teaches that a (RAE) in which a diffraction grating comprises a dispersive optics system element, which diffraction grating is situated prior to a detector element and serves to provide a multiplicity of independently detectable light wavelength beams to said detector element, should have (PDS) response wavelength dependence reduced by application of a specific system element to said (RAE), and by practice of a specific method of use thereof. The present invention method of use includes the teaching that compensation of said (RAE) (PDS) can be further effected by mathematical application of ALPHA and BETA correction factors, or by direct mathematical correction of PSI and DELTA values.

A search of relevant references has provided an article by Russev, App. Optics, Vol. 28, No. 8, April 1989, p. 1504–1507. An approach to mathematically calculating ALPHA and BETA correction factors to compensate for (PDS) and/or detecting system nonlinearity, either independently or simultaneously, is described in said reference. As well, said reference mentions the use of a depolarizer between a rotating analyzer and a detector as a means of reducing (PDS), but notes that said approach is not complete because of residual beam polarization. In addition, the presence of a depolarizer is stated to be undesirable because it reduces light flux reaching the detector.

In view of the approach described in the Russev reference, it is noted that an article by Johs, Thin Solid Films, 234(1993), p. 395–398, describes an improved approach to determining and applying ALPHA and BETA correction factors using a regression data fitting approach over a large range of polarizer azimuth angles.

The Russev and Johs articles cited above are incorporated by reference into this Disclosure.

A U.S. Pat. No. 4,837,603 to Hayashi, describes a method of correcting azimuth angle of photometric ellipsometers by an approach which mathematically corrects PSI and DELTA. Said reference is also incorporated by reference into this Disclosure.

An article by Stobie et al., J. Opt. Soc. Am. 65, p. 25 (1975), describes application of a double modulation which could be used to circumvent (PDS) of dispersive optics. The system requires that a polarizer, (ie. polarization state generator), and an analyzer (ie. polarization state detector), be set at known azimuths, and that a rotating analyzer, (ie. modulator), be present before or after a sample. As it is difficult, however, to determine azimuths of a polarizer and analyzer, their being nonlinear functions of ellipsometric measurement parameters, use of the ellipsometer system described in said reference is relatively complex and in some applications unsuitable for application to spectroscopic ellipsometer systems because sensitivity to certain values of PSI and DELTA is reduced. It is noted that the Stobie et al. article fails to suggest that the system described therein should be used to compensate (PDS).

An article by Collins, Rev. Scien. Inst., 61(8), August 1990, p. 2029–2062, describes an ellipsometer system which uses a rotating polarizer. Said system could be used to remove (PDS) of dispersive optics but introduces (PDS) to the system light source. In said system an analyzer is set at a known azimuth and modulation is introduced in the polarization state generator. Said configuration requires calibration of residual light source polarization, and light beam precession on the sample can occur during use. This is especially unsuitable wherein monitoring of a real time, in situ process is involved. As well, the Collins article fails to suggest use of the system described therein to compensate (PDS).

The above discussion should serve to demonstrate that a system, and method of use thereof, which can easily, simply and efficiently serve to reduce (PDS), and which does not impose any unnecessary restraints on (PDS) reducing system element design or configuration, would provide utility. Such a system and method of use are taught by the present invention.

DISCLOSURE OF THE INVENTION

The present invention assumes the presence of a Rotating Analyzer Ellipsometer System, (RAE). Briefly, a (RAE) is comprised of a sequential functional combination of a Light Source, (LS) and a Polarization State Generator, (PSG). Said (RAE) is further comprised of a sequential functional combination of a Rotating Analyzer, (RA), a Dispersive Optics, (eg. a Diffraction Grating (DG)), and a Photodetector Array, (PA).

In use said (LS) provides a beam of polychromatic light to said (PSG) and said (PSG) effects an intended polarization state thereof. Said beam of polychromatic light in said intended polarization state is then caused to interact with, and reflect from, a Substrate System, (SS), which interaction causes an alteration in the polarization state of said beam of polychromatic light. Said altered polarization state beam of polychromatic light is then caused to pass through said (RA) and emerge as linearly polarized. Said linearly polarized beam of polychromatic light is then caused to interact with and reflect from said (DG) whereat a diffracted multiplicity of essentially single wavelength beams of typically elliptically polarized light are caused to form, each of which essentially single wavelength beam of typically elliptically polarized light is caused to be directed so as to enter a separate Detector Element, (DE), of said (PA). Said (DE's) are oriented at predetermined angles with respect to said (DG) and said (DG) can be rotated to set the angle of incidence of said linearly polarized beam of light thereon, with respect to a normal to said (DG), to within plus or minus one-half (0.5) a degree. Said (DE's) are typically, but not necessarily, photodiodes which can provide essentially linear output signal verses input light intensity characteristics over an operating wavelength spectra. Each of said (DE's) serve to detect the intensity of a received, essentially single wavelength beam of typically elliptically polarized light entering thereto, as a function of time. Proper analysis of said intensity verses time data can provide PSI and DELTA constants, (at the specific light beam wavelength detected by a (DE)), of a (SS), as described in the Background Section of this Disclosure. A problem in the operation of the described (RAE) exists, however, in that said (DG) causes different effects on linearly polarized light beams of different wavelengths. That is, the (DG) introduces Polarization-Dependent Sensitivity (PDS) error. The present invention is in part an additional (RAE) system element, termed a Stationary Compensator, (SC), which in combination with a Rotating Analyzer (RA) comprises a Rotating Analyzer Stationary Compensator Assembly system (RASCA), the presence of which in said (RAE), during use thereof, serves to reduce (DG) introduced (PDS) error.

The present invention teaches that a (RAE) should be modified so as to functionally include a Stationary Compensator, (SC), such that during use the "fast axis" of said (SC) is in a fixed orientation with respect to grooves in said (DG), said combination of (RA) and (SC) effecting a functional Rotating Analyzer-Stationary Compensator Assembly system, (RASCA). Said (RASCA) is typically realized as a functionally related system comprised of a physically independent (RA) and a physically independent (SC), thereby allowing use of a compensator of any functional gemetric shape.

The purpose of said (RASCA) is to accept a polychromatic beam of typically elliptically polarized light, provide linearly polarized light emerging from said (RA), and cause said linearly polarized light to be converted to a polychromatic beam of light in an elliptical, preferably essentially circularly, polarized form, prior to being caused to interact with and reflect from, in a diffracted form, said (DG) as a multiplicity of essentially single wavelength elliptically polarized beams of light.

The surprising end effect of the presence of said (SC) in said (RASCA), and the incorporated method of its use, is to reduce (PDS) introduced by said (DG) because the (DG) does not introduce as much (PDS) to an elliptically polarized beam of light as it does to a linearly polarized beam of light. That is, the (DG) operates, (eg. rotates light beam components), more consistently over a spectrum of wavelengths when incident elliptically polarized beams of light are present, than it does over the same spectrum of wavelengths when incident linearly polarized beams of light are present.

The present invention also teaches that Fourier Coefficient, ALPHA and BETA, correction factors as mentioned in the Background Section and references cited therein (eg. Russev and Johs articles), can be derived for each essentially single wavelength of elliptically polarized light, and applied to measured ALPHA and BETA values, to effect full (PDS)

compensation. When this is done a correction factor application means, (eg. a computing system), in combination with said (RAE), is utilized. Briefly, a series of raw ALPHA and BETA values are measured as a function of a series of (PSG) azimuths. An equation is then fit to said data utilizing a Mean Square Error criteria to obtain corrected ALPHA and BETA. The signals measured by the (DE's) are of the form:

$$I_D(t)=I_0(1+\alpha_{measured}\cos 2\omega t+ \beta_{measured} \sin 2\omega t)$$

For a "perfect" or ideal system the following equations predict the normalized Fourier Coefficients, as a function of ellipsometric parameters of the sample (eg. PSI and DELTA), the normalized input polarizer angle (P), and the azimuthal offset or calibration angle for the input polarizer (Ps):

$$\alpha_{ideal} = \frac{\tan^2\Psi - \tan^2(P - Ps)}{\tan^2\Psi + \tan^2(P - Ps)}$$

$$\beta_{ideal} = \frac{2\tan\Psi \cos\Delta}{\tan^2\Psi + \tan^2(P - Ps)}$$

The first correction to these coefficients is due to (PDS). The magnitude of the (PDS) at a particular wavelength is given by "f", and the azimuthal angle of the (PDS) is given by "Fd". Denoting:

$$x=(1-f^2)/(1+f^2)$$

$$x_c=x \cos(2 F_d)$$

$$x_s=x \sin(2 F_d)$$

The (PDS) corrections are then applied to the ideal coefficients:

$$\alpha'=(\alpha_{ideal}+x_c)/[1+0.5(\alpha x_c+\beta x_s)]$$

$$\beta'=(\beta_{ideal}+x_s)/[1+0.5(\alpha x_c+\beta x_s)]$$

Finally, the standard (RAE) calibration constants for the analyzer azimuth (As) and the electronic attenuation factor (η) are introduced to complete the calculation of the predicted Fourier Coefficients, which should be the same as the measured Fourier Coefficients, when all of the calibration constants have been accurately determined:

$$\alpha_{measured}=\alpha_{predicted}=(1/\eta)[\alpha'\cos(2 As)-\beta' \sin(2 As)]$$

$$\beta_{measured}=\beta_{predicted}=(1/\eta)[\alpha'\sin(2 As)+\beta'\cos(2 As)]$$

Similarly, mathematical correction of PSI and DELTA values can be performed, such as described in U.S. Pat. No. 4,837,603, for instance.

The present invention will be better understood by reference to the Detailed Description Section of the present Disclosure, in conjunction with the Drawings.

SUMMARY OF THE INVENTION

Rotating Analyzer Ellipsometry (RAE) systems which utilize polychromatic light and which utilize dispersive optics to simultaneously provide a multiplicity of essentially single wavelength beams of light to separate Detector Elements (DE) in a Photodetector Array (PA) for analysis thereof, are known.

A problem associated with use of said (RAE's) is that dispersive optics, (eg. Diffraction Grating (DG)), therein introduce Polarization-Dependent Sensitivity (PDS). This is particularly true when polychromatic light diffracted thereby is other than essentially circularly polarized. That is, (PDS) effected by dispersive optics is less pronounced when light incident thereon is essentially circularly polarized, or at least elliptically polarized, than when it is in a linearly polarized state.

One approach to compensating (PDS) is by application of mathematical correction factors applied to ALPHA and BETA Fourier coefficients, (which correction factors and ALPHA and BETA values are derived from analysis of (RAE) provided data), prior to calculating Substrate System (SS) characterizing PSI and DELTA parameter values from corrected ALPHA and BETA. Use of a purely mathematical approach, however, results in reduced sensitivities at certain PSI and DELTA values because ALPHA and/or BETA correction factors can represent a rather significant percentage of a raw ALPHA and/or BETA at said corresponding PSI and DELTA values. Application of said correction factors then provides rather small corrected ALPHA and/or BETA values which can be rather more adversely affected by system noise. Mathematical correction of PSI and DELTA values can also be practiced, with similar accompanying problems.

Another approach to reducing (PDS) is to provide light to a (DG) which is elliptically, and preferably essentially circularly polarized, as opposed to linearly polarized. The present invention teaches that this should be accomplished by effecting a functional combination of a Rotating Analyzer (RA) and a Stationary Compensator (SC) to form a Rotating Analyzer Stationary Compensation Assembly System (RASCA) in a (RAE) such that a light beam entering said (RA), after being reflected from a Sample Substrate (SS), exits said (SC) in an elliptically, (preferably essentially circularly), polarized state prior to being diffracted by said (DG).

The present invention provides that both identified approaches, (ie. use of said (RASCA) and mathematical), to reducing (PDS), can be utilized.

It is therefore a purpose of the present invention to identify an improved (RAE).

It is another purpose of the present invention to identify an improved (RAE) in which a (DG) serves as dispersive optics and in which (PDS) compensation can be relatively easily accomplished.

It is yet another purpose of the present invention to teach a relatively simple (RAE) system element in the form of a (SC) which, in functional combination with a (RA), comprises a (RASCA), which (RASCA) during use, provides elliptically, (preferably essentially circularly), polarized light to a (DG) in the containing (RAE).

It is still yet another purpose of the present invention to teach the use of a mathematical approach to compensating (PDS) in a (RAE) which includes a (RASCA).

DETAILED DESCRIPTION

Figure 1:
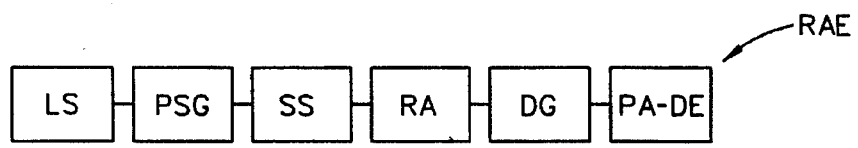
FIG. 1 shows a block diagram of a rotating analyzer ellipsometer system.
Figure 6:
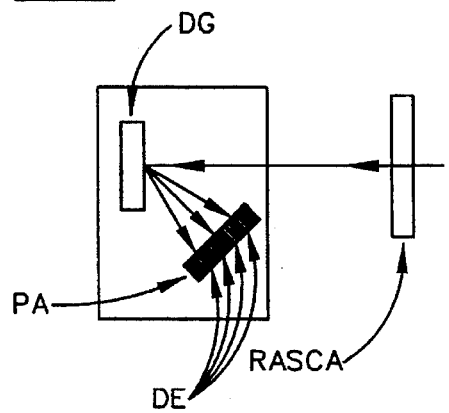
FIG. 6 shows the relative orientation of a diffraction grating and a photodetector array, which photodetector array is shown to be comprised of a multiplicity of detector elements.

Turning now to the Drawings, there is shown in FIG. 1 a Rotating Analyzer Ellipsometer System (RAE) as disclosed in copending patent application Ser. No. 07/947,430 now U.S. Pat. No. 5,373,359. Identified are Light Source (LS), Polarization State Generator (PSG), Sample Substrate (SS), Rotating Analyzer (RA), Diffraction Grating (DG), and Photodetector Array (PA). FIG. 6 shows the relative orientation of diffraction grating (DG) and photodetector array (PA), which photodetector array (PA) is comprised of a multiplicity of Detector Elements (DE's). It is noted that said Diffraction Grating (DG) is pivotably mounted so that it can receive incident light at desired angles with respect to the normal thereto, said angles being controllable to plus or minus one-half (0.5) a degree.

In use Light Source (LS) provides typically polychromatic light in a typically collimated form to said Polarization State Generator (PSG), from which a typically polychromatic collimated beam of light emerges in an intended polarization state. (Note, said polychromatic typically colliminated light can be carried from the (LS) to the (PSG) by a light fiber (LF) in one, nonlimiting, embodiment of the present invention). Said typically collimated polychromatic beam of light is then caused to impinge upon said Sample Substrate (SS), and reflect therefrom in an altered state of polarization. Said reflected altered polarization state beam of light reflecting from said Sample Substrate (SS) is then caused without further focusing, to pass through said Rotating Analyzer (RA) from which it emerges in a linearly polarized form, then reflects from said Diffraction Grating (DG) in a diffracted state comprising a multiplicity of essentially single wavelength typically elliptically polarized beams of light; at least some of which are caused to enter specific wavelength associated Detector Elements (DE's) in said Photodetector Array (PA), wherein analysis of the intensity thereof is performed with respect to time. It is noted that Photodetector Array (PA) Detector Elements (DE's) which have linear intensity verses signal output characteristics, such as photodiodes, are preferred. Utilizing said linear characteristic Detector Elements (DE's) eliminates complications associated with use of, for instance, photomultiplier tubes as detectors.

While the above described Rotating Analyzer Ellipsometer system (RAE) provides benefits, a problem has been found to exist during use in that said Diffraction Grating (DG) introduces wavelength sensitive Polarization-Dependent Sensitivity (PDS). That is, the Diffraction Grating (DG) responds differently to linearly polarized light of different wavelengths, and introduces different Polarization-Dependent Sensitivity (PDS) errors to the various of said multiplicity of essentially single wavelength typically elliptically polarized beams of light diffracted therefrom.

A mathematical approach to compensating said Polarization-Dependant Sensitivity (PDS) involves obtaining and applying correction factors to ALPHA and BETA Fourier Coefficients derived by applying Fourier Analysis to raw data obtained from Photodetector Array (PA) Detector Elements (DE's), prior to calculating Sample Substrate (SS) constants PSI and DELTA for each detected essentially single wavelength typically elliptically polarized beam of light. (Note that PSI and DELTA values are calculated from corrected ALPHA and BETA's). This approach is better described in Background Section cited references, (eg. Russev and Johs articles), which are incorporated herein by reference. As well, PSI and DELTA values can be directly mathematically corrected by an approach, for instance, as described in U.S. Pat. No. 4,837,603 also referenced in the Background Section of this Declaration.

Figure 2:
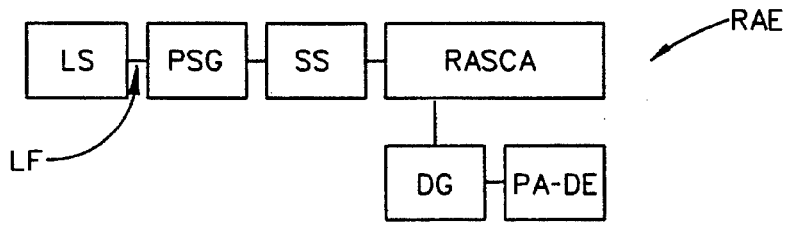
FIG. 2 shows a block diagram of a rotating analyzer ellipsometer system which includes a stationary compensator in functional combination with a rotating analyzer.
Figure 3:
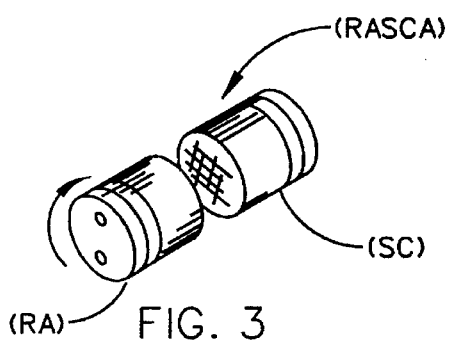
FIG. 3 shows a perspective representation of a rotating analyzer in functional combination with a stationary compensator.

The present invention, however, teaches that Polarization-Dependent Sensitivity (PDS) should be simultaneously reduced in a multiplicity of essentially single wavelength beams of light reflected and diffracted from said Diffraction Grating (DG), by addition of an element to the Rotating Analyzer Ellipsometer System (RAE) of FIG. 1. Said additional element is termed a Stationary Compensator (SC) and is indicated in FIG. 2 as being part of a functional combination of a Rotating Analyzer (RA) and said Stationary Compensator (SC), which together comprise a Rotating Analyzer Stationary Compensator Assembly System (RASCA). FIG. 3 better shows that said Rotating Analyzer Stationary Compensator Assembly System (RASCA) is comprised of a Rotating Analyzer (RA) and a Stationary Compensator (SC) in fixed geometric functional relationship to one another. In use a beam of light entering said Rotating Analyzer (RA) passes therethrough, then passes through said Stationary Compensator, (SC) prior to being caused to impinge upon and reflect from, in a diffracted form, said Diffraction Grating (DG). It will be recalled that light exiting said Rotating Analyzer (RA) is linearly polarized. The purpose of the Stationary Compensator (SC) is to alter said polarization state thereof to elliptical, and preferably, to essentially circular. The reason being that a Diffraction Grating (DG) introduces less Polarization-Dependent Sensitivity (PDS) to elliptically and essentially circularly polarized light than it does to linearly polarized light. It is also to be understood that Detector Elements (DE) can introduce Polarization-Dependent Sensitivity in a Rotating Analyzer Ellipsometer System (RAE). The present invention system and method can also be utilized to compensate such. It is emphasized that the described Rotating Analyzer Stationary Compensator Assembly system (RASCA), and the method of its use in a Rotating Analyzer Ellipsometer (RAE) are focuses of the present invention.

Figure 4:
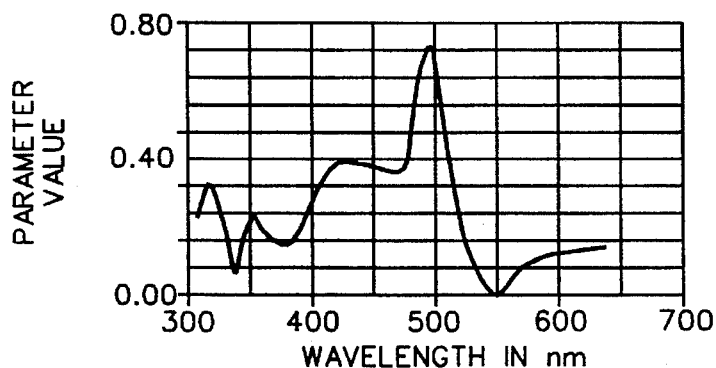
FIG. 4 shows a graph of polarization-dependence sensitivity as a function of light beam wavelength in a rotating analyzer ellipsometer which does not include a stationary compensator as indicated in FIG. 1.
Figure 5:
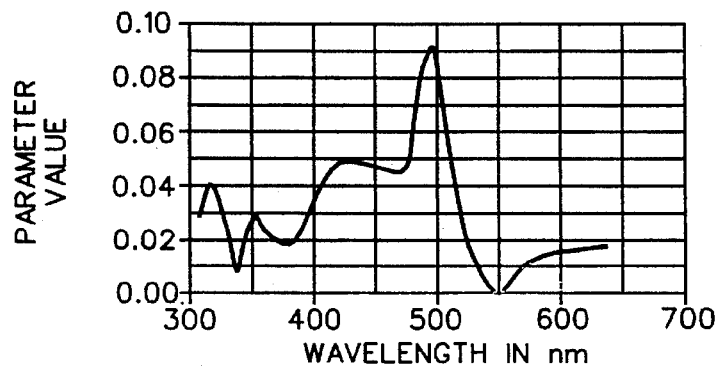
FIG. 5 shows a graph of polarization-dependence sensitivity as a function of light beam wavelength in a rotating analyzer ellipsometer which includes a stationary compensator as indicated in FIG. 2.

Turning now to FIG. 4, there is provided a graph of Polarization-Dependent Sensitivity (PDS) verses Light Beam Wavelength provided by a Rotating Analyzer Ellipsometer System (RAE) as shown in FIG. 1. FIG. 5 shows a similar graph of Polarization-Dependent Sensitivity (PDS) for a Rotating Analyzer Ellipsometer System (RAE) as shown in FIG. 2. The attenuation reduction in Polarization-Dependent Sensitivity (PDS) demonstrated in FIG. 5 as compared to FIG. 4, (peaked at a light beam wavelength of approximately five-hundred (500) Nanometers for the example shown), is a direct result of the presence of the Stationary Compensator (SC) identified in FIGS. 2 and 3.

It is noted that a suitable Stationary Compensator (SC) can be embodied using Melles Griot or CVI Optics Corporation quarter wavelength, (ninety (90) degree), Mica Retardation Plates. For example Melles Griot Product No. 02

Figure 7:
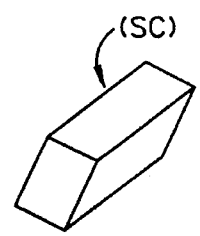
FIG. 7 shows a rhomboid shaped stationary compensator suitable for use in the present invention.

WRM 001 or 02 WRM 011 and the like are identified. As well, Freshnel Rhomb Retarders, as available from Lambrecht Co. or Oriel Co., (Product Numbers FRS4-10-BB, FRS4-15-BB, FR94-20-BB for instance), can be utilized. FIG. 7 shows the general shape of a Freshnel Rhomb Retarder. Note that the geometrical shape thereof would preclude convenient attachment to a rotating analyzer. That is, that the compensator is stationary allows use of a wide variety of compensator geometries as a result.

The present invention teaches that the mathematical approach to compensating for Polarization-Dependent Sensitivity (PDS) mentioned above can also be applied to Fourier Coefficients obtained from analysis of data provided by the present invention embodiment which includes the Stationary Compensator (SC), as indicated in FIG. 2. It is therefore to be appreciated that the method of the present invention provides that further Polarization-Dependent Sensitivity compensation by mathematical correction of Fourier Coefficients APLHA and BETA described elsewhere in this Disclosure can be applied to data represented in FIG. 5 to provide fully compensated Polarization-Dependent Sensitivity (PDS). The benefit provided by the presence of the stationary compensator (sc) of the present invention then, is that its use greatly reduces required mathematical compensation. As described in the Background Section, this decreases PSI and DELTA reduced sensitivity problems.

It is mentioned that the terminology "Substrate System" and "(SS)" have been used throughout this Disclosure. Said terminology is to be understood to include any substrate, with or without one or more films atop thereof, and any container for a substrate etc. which can be analyzed by a (RAE).

The terminology "Photodetector Array" and "(PA)" has also been used throughout the Disclosure. Said terminology is to be understood to include, but is not limited to, Photodiode Arrays.

The terminology "Rotating Analyzer" is to be understood to mean a rotating polarization analyzer.

The terminology "Stationary Compensator" is to be understood to mean for instance, a ninety (90) degree, (ie. quarter wavelength), retardation plate, a freshnel rhomboid retarder or any functionally similar system.

The terminology "Diffraction Grating" amd "(DG)" are used throughout this disclosure. It is to be understood that said terminology identifies a particularly relevant, but not limiting, example of a Dispersive Optics.

The terminology "essentially single wavelength" has been used throughout this disclosure. It is to be understood that light from a Dispersive Optics is a continuum of wavelengths, but that physical restraints on detecting such by necessity involves Finite Dimension Detector Elements, each of which detects a small range of wavelengths in said continuum thereof, which small range of wavelengths is centered at some wavelength. The terminology "essentially single wavelength" refers to said wavelength about which the small range of wavelengths is centered, in combination with the immediately surrounding slightly larger or smaller wavelengths. In the limit, an essentially "single" wavelength could be theoretically envisioned as present.

In addition, it is to be understood that the terminology "Polychromatic Light" is inclusive of White Light.

Finally, the terminology "essentially circular" has been used throughout this Disclosure. As the difference between "essentially circular" and "elliptical", as said terms are understood by those skilled in the art of ellipsometry is subjective and open to interpretation, it is to be understood that said terminology should be interpreted, where appropriate, to mean "elliptical" with the optimum state being "circular".

Having hereby disclosed the subject matter of the present invention, it should be obvious that many modifications, substitutions and variations of the present invention are possible in light of the teachings. It is therefore to be understood that the present invention can be practiced other than as specifically described, and should be limited in breadth and scope only by the claims.

We claim:

1. A spectroscopic ellipsometer for use in sensing characteristics of a sample substrate system comprising:
    a. a light source;
    b. a polarization state generator;
    c. an analyzer; and
    d. a diffraction grating positioned so as to receive a beam of polychromatic light which passes through the analyzer without further focusing after said beam of polychromatic light, which originates in said light source, reflects from a substrate system; wherein said diffraction grating reflects incident polychromatic light onto a photodetector array at a predetermined angle with respect to the normal to the diffraction grating, with a precision of at least plus or minus one-half degree, in which spectroscopic ellipsometer light is carried from said light source to said polarization state generator by a light fiber.

2. A spectroscopic ellipsometer for use in sensing characteristics of a sample substrate system comprising:
    a. a light source;
    b. a polarization state generator;
    c. an analyzer; and
    d. a diffraction grating positioned so as to receive a beam of polychromatic light which passes through the analyzer without further focusing after said beam of polychromatic light, which originates in said light source, reflects from a substrate system; wherein said diffraction grating reflects incident polychromatic light onto a photodetector array at a predetermined angle with respect to the normal to the diffraction grating, with a precision of at least plus or minus one-half degree, in which spectroscopic ellipsometer said polychromatic beam of light which passes through said analyzer is caused to pass through a stationary compensator and emerge therefrom as other than a linearly polarized polychromatic beam of light prior to reflecting in a diffracted form from said diffraction grating.

3. A rotating analyzer ellipsometer system comprising:
    a. a light source;
    b. a polarization state generator;
    c. a rotating analyzer;
    d. a diffraction grating; and
    e. a photodetector system;

such that, during use, a beam of polychromatic light from said light source is caused to pass through said polarization state generator and is then caused to be reflected from a substrate system, thereby becoming a typically elliptically polarized beam of light; such that said typically elliptically polarized polychromatic beam of light is, without further focusing, caused to pass through said rotating analyzer and become linearly polarized, which linearly polarized polychromatic beam of light emerging from said rotating analyzer is then caused to be incident upon said diffraction grating at an intended angle to a normal thereto, precise to plus or minus one-half degree, and reflect in a diffracted form therefrom as a multiplicity of essentially single wavelength beams of light, each of which essentially single wavelength beams of light enters a separate detector element of said photodetector system for analysis therein, in which rotating analyzer ellipsometer system light is carried from said light source to said polarization state generator by a light fiber.

4. A rotating analyzer ellipsometer system comprising:
   a. a light source;
   b. a polarization state generator;
   c. a rotating analyzer;
   d. a diffraction grating; and
   e. a photodetector system;
such that, during use, a beam of polychromatic light from said light source is caused to pass through said polarization state generator and is then caused to be reflected from a substrate system, thereby becoming a typically elliptically polarized beam of light; such that said typically elliptically polarized polychromatic beam of light is, without further focusing, caused to pass through said rotating analyzer and become linearly polarized, which linearly polarized polychromatic beam of light emerging from said rotating analyzer is then caused to be incident upon said diffraction grating at an intended angle to a normal thereto, precise to plus or minus one-half degree, and reflect in a diffracted form therefrom as a multiplicity of essentially single wavelength beams of light, each of which essentially single wavelength beams of light enters a separate detector element of said photodetector system for analysis therein; which rotating analyzer ellipsometer system further comprises a stationary compensator in functional combination with said rotating analyzer; such that said linearly polarized polychromatic beam of light which emerges from said rotating analyzer is caused to pass through said stationary compensator and emerge therefrom as other than a linearly polarized polychromatic beam of light prior to reflecting in a diffracted form from said diffraction grating.

5. A rotating ,analyzer ellipsometer system as in claim 4 in which a fast axis of the stationary compensator is oriented at an intended angle with respect to grooves in the diffraction. grating.

6. A rotating analyzer ellipsometer system as in claim 5 in which the intended angle is forty-five (45) degrees.

7. A rotating analyzer ellipsometer system as in claim 5 in which the intended angle is other than forty-five (45) degrees.

8. A rotating analyzer ellipsometer system as in claim 4 in which the Rotating Analyzer and Stationary Compensator comprise a single element functional combination.

9. A rotating analyzer ellipsometer system as in claim 4 in which light emerging from said stationary Compensator during use is essentially circularly polarized.

10. A rotating analyzer ellipsometer system comprising:
    a. a light source;
    b. a polarization state generator;
    c. a rotating analyzer;
    d. a dispersive optic; and
    e. a photodetector system;
such that, during use, polychromatic light from said light source is caused to pass through said polarization state generator and is then caused to reflect from a substrate system, thereby becoming a typically elliptically polarized beam of light; such that said typically elliptically polarized polychromatic light is, without further focusing, caused to pass through said rotating analyzer and become essentially linearly polarized, which essentially linearly polarized polychromatic light emerging from said rotating analyzer is then caused to be incident upon said dispersive optics at an intended angle to a normal thereto, and be directed therefrom at an angle with respect to a normal thereto which is precise to within plus or minus one-half a degree, and proceed therefrom as a multiplicity of essentially single wavelength beams of light, each of which essentially single wavelength beam of light enters a separate detector element of said photodetector system for analysis therein, in which rotating analyzer ellipsometer system light is carried from said light source to said polarization state generator by a light fiber.

11. A rotating analyzer ellipsometer as in claim 10 in which the photodetector system is a photodiode array comprising a plurality of detector elements.

12. A rotating analyzer ellipsometer system comprising:
    a. a light source;
    b. a polarization state generator;
    c. a rotating analyzer;
    d. a dispersive optic; and
    e. a photodetector system;
such that, during use, polychromatic light from said light source is caused to pass through said polarization state generator and is then caused to reflect from a substrate system, thereby becoming a typically elliptically polarized beam of light; such that said typically elliptically polarized polychromatic light is, without further focusing, caused to pass through said rotating analyzer and become essentially linearly polarized, which essentially linearly polarized polychromatic light emerging from said rotating analyzer is then caused to be incident upon said dispersive optics at an intended angle to a normal thereto, and be directed therefrom at an angle with respect to a normal thereto which is precise to within plus or minus one-half a degree, and proceed therefrom as a multiplicity of essentially single wavelength beams of light, each of which essentially single wavelength beam of light enters a separate detector element of said photodetector system for analysis therein; which rotating analyzer ellipsometer system further comprises a stationary compensator in functional combination with said rotating analyzer, such that said essentially linearly polarized polychromatic light which emerges from said rotating analyzer is caused to pass through said stationary compensator and emerge therefrom as other than lineraly polarized prior to encountering said dispersive optics.

13. A rotating analyzer ellipsometer system as in claim 12 in which a fast axis of the stationary compensator is oriented at an intended angle with respect to grooves in the dispersive optics.

14. A rotating analyzer ellipsometer system as in claim 13 in which the intended angle is forty-five (45) degrees, 15. A rotating analyzer ellipsometer system as in claim 13 in which the intended angle is other than forty-five (45) degrees, 16. A rotating analyzer ellipsometer system as in claim 12 in which the Rotating Analyzer and Stationary Compensator comprise a single element functional combination.

17. A rotating analyzer ellipsometer system as in claim 12 in which light emerging from said stationary Compensator during use essentially circularly polarized.

18. A rotating analyzer ellipsometer as in claim 12 in which the photodetector system is a photodiode array comprising a plurality of detector elements, 19. A method of reducing polarization-dependence sensitivity of dispersive optics in rotating analyzer ellipsometer systems, comprising the steps of:

a. providing a rotating analyzer ellipsometer system comprising:
   a. a light source;
   b. a polarization state generator;
   c. a rotating analyzer;
   d. a stationary compensator;
   e. a dispersive optics; and
   f. a photodetector system;

such that, during use, polychromatic light from said light source is caused to pass through said polarization state generator and is then caused to reflect from a substrate system, thereby becoming typically elliptically polarized light; such that said typically elliptically polarized polychromatic light is, without further focusing, caused to pass through said rotating analyzer and become essentially linearly polarized, which essentially linearly polarized polychromatic light emerging from said rotating analyzer is then caused to pass through said stationary compensator, such that said linearly polarized light which exits said rotating analyzer is caused, by passage through said stationary compensator, to become other than linearly polarized, which other than linearly polarized beam of light which emerges from said stationary compensator is then caused to interact with said dispersive optics and emerge therefrom as a multiplicity of essentially single wavelength beams of light, each of which enters a separate detector element of said photodetector system for analysis therein;

b. causing polychromatic light to emerge from said light source and reflect from said substrate system, proceed through said rotating analyzer and stationary compensator, without further focusing after reflecting from said substrate system, and interact with said dispersive optics such that a multiplicity of essentially single wavelength, other than linearly polarized, beams of light are produced and directed from said dispersive optics at an angle with respect to a normal thereto which is precise to within plus or minus one-half a degree; and c. causing at least some of said multiplicity of essentially single wavelength, other than linearly polarized beams of light produced to enter said photodetector system for analysis therein.

20. A method of reducing polarization-dependence sensitivity of dispersive optics in rotating analyzer ellipsometer systems as in claim 19, which further comprises the steps of:

a. additionally sensing at least some of said multiplicity of other than linearly polarized beams of light which emerge from said dispersive optics, and determining mathematical correction factors based thereon; and b. utilizing said mathematical correction factors via correction factor application means, to mathematically correct polarization-dependent sensitivity.

* * * * *